(12) United States Patent
Curtis et al.

(10) Patent No.: US 12,054,314 B2
(45) Date of Patent: Aug. 6, 2024

(54) ORAL CARE PRODUCT

(71) Applicant: The Procter & Gamble Company, Cincinnati, OH (US)

(72) Inventors: Michael David Curtis, Mason, OH (US); Niranjan Ramji, Mason, OH (US); Franco Silva Medeiros, Loveland, OH (US); Natalia Maria Ramon Martinez, West Chester, OH (US); Jayanth Rajaiah, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 443 days.

(21) Appl. No.: 17/410,279

(22) Filed: Aug. 24, 2021

(65) Prior Publication Data

US 2022/0054373 A1 Feb. 24, 2022

Related U.S. Application Data

(60) Provisional application No. 63/069,660, filed on Aug. 24, 2020.

(51) Int. Cl.
*B65D 35/02* (2006.01)
*A46B 3/22* (2006.01)
*A46B 11/00* (2006.01)
*A61C 19/06* (2006.01)
*A61K 8/06* (2006.01)
(Continued)

(52) U.S. Cl.
CPC ............... *B65D 35/02* (2013.01); *A46B 3/22* (2013.01); *A61C 19/066* (2013.01); *A61K 8/06* (2013.01); *A61Q 11/00* (2013.01); *B65D 35/36* (2013.01); *A46B 11/002* (2013.01); *A61K 2800/87* (2013.01)

(58) Field of Classification Search
CPC ...... A61K 8/06; A61K 2800/87; B65D 35/02; B65D 25/36; A61Q 11/00; A46B 3/22; A46B 11/00; A46B 11/001; A46B 11/0041; A46B 9/005; A61C 19/066
USPC ......................................... 401/268, 270, 282
See application file for complete search history.

(56) References Cited

U.S. PATENT DOCUMENTS

2005/0069372 A1\* 3/2005 Hohlbein ............. A61B 17/244
401/282
2012/0257920 A1 10/2012 Jimenez et al.
(Continued)

OTHER PUBLICATIONS

PCT Search Report and Written Opinion for PCT/US2021/047240 dated Jan. 5, 2022, 15 pages.

*Primary Examiner* — David J Walczak
(74) *Attorney, Agent, or Firm* — Elizabeth A. Conklin

(57) ABSTRACT

An oral care product comprises a package comprising a container and an applicator tip attached to the container. The applicator tip comprises a material having a Shore A hardness of from about 15 to about 80 and has a dispensing orifice in fluid communication with the container. The dispensing orifice has a minimum diameter of at least about 0.5 mm, preferably at least about 1 mm. The oral care product further comprises an oral care composition contained within the container of the package, wherein the oral care composition comprises an oral care active and has a cone penetration value of from about 10 to about 500, preferably from about 100 to about 300.

27 Claims, 3 Drawing Sheets

(51) Int. Cl.
 *A61Q 11/00* (2006.01)
 *B65D 35/36* (2006.01)

(56) References Cited

U.S. PATENT DOCUMENTS

2018/0133119 A1 5/2018 Rajaiah
2023/0172819 A1 6/2023 Rajaiah et al.

* cited by examiner

ORAL CARE PRODUCT

FIELD OF THE INVENTION

The present invention relates to an oral care product comprising an oral care composition contained within a container of a package, wherein the package comprises an applicator tip attached to the container.

BACKGROUND OF THE INVENTION

Currently in the marketplace are dental products by which various cosmetic and/or therapeutic actives are delivered to teeth and the oral cavity. Examples of such products include: brushing aids, such as dentifrice products for delivery of oral care actives for example polyphosphates or fluorides; mouthwashes containing breath fresheners or antibacterial actives; and whitening strips for the delivery of bleaching actives to the teeth. In particular, the use of a dental strip has been recognized as a convenient and inexpensive way to deliver cosmetic and therapeutic benefits to the teeth and mucosal surfaces of the oral cavity; for example, dental whitening strips, where a whitening composition is applied to a strip and thereafter applied to the teeth to achieve sustained contact between the teeth and the whitening composition.

Despite the above known approaches for the treatment of oral conditions, especially for leave-on compositions for treating or whitening teeth, a need still exists for providing improved oral care products with enhanced convenience for consumers along with acceptable product performance and ease of application to teeth. With respect to convenience, consumers desire an oral care product that can be used on-the-go and carried in a pocket, briefcase, handbag or travel bag. There thus remains a desire for products having enhanced convenience and preference for the consumer, while maintaining sufficient performance and ease of application.

SUMMARY OF THE INVENTION

Oral care products of the present invention comprise packaging comprising an applicator tip attached to a container containing an oral care composition. The applicator tip comprises a material having a Shore A hardness of from about 15 to about 80. The applicator tip has a dispensing orifice in fluid communication with the container, wherein the dispensing orifice has a minimum diameter of at least about 0.5 mm, preferably at least about 1 mm. The oral care composition, contained within the container of the package, comprises an oral care active and has a cone penetration value of from about 10 to about 500, preferably from about 100 to about 300. The oral care composition of the present invention is able to be easily dispensed from the package and applied to a consumer's teeth with improved spreading and evenness.

DETAILED DESCRIPTION OF THE INVENTION

Definitions

Figure 1A:
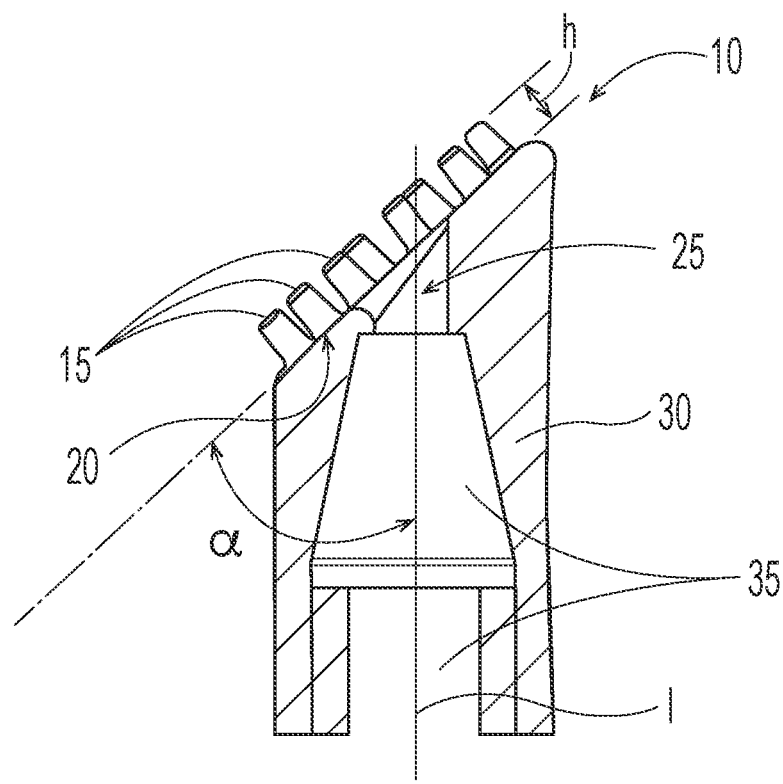
FIG. 1A is a cross-sectional view of an embodiment of an applicator tip of the present invention.

By "oral care composition" or "oral care product", as used herein, is meant a product, which in the ordinary course of usage, is not intentionally swallowed for purposes of systemic administration of particular therapeutic agents, but is rather retained in the oral cavity for a time sufficient to contact dental surfaces or oral tissues. Examples of oral care compositions include tooth gel, subgingival gel, mousse, foam, breath freshening compositions, or denture care or adhesive product. "Oral care compositions" or "oral care products" do not include products for treating or applying to lips. Preferred oral care products or compositions include tooth whitening products or compositions. The oral care composition may also be incorporated onto strips or films for direct application or attachment to oral surfaces.

The term "leave-on composition", as used herein, includes tooth or subgingival pastes, gels, or liquid formulations unless otherwise specified, which are applied to teeth and allowed to remain on the teeth, preferably for a prescribed period of time, without being rinsed from the teeth.

The term "phase" as used herein means a physically distinct region or regions, which may be continuous or discontinuous, having one or more properties that are different from another phase. Non-limiting examples of properties that may be different between phases include composition, viscosity, solubility, hydrophobicity, hydrophilicity, and miscibility.

The term "multi-phase oral composition" as used herein comprises a mixture of two or more phases that are immiscible with each other. The phases may be continuous, discontinuous, or combinations thereof. Examples of multi-phase oral compositions include emulsions, such as water in oil emulsions. Examples of multi-phase oral compositions also include oil-in-water emulsions, water-in-oil-in-water emulsions, and oil-in-water-in-oil emulsions. Examples of multi-phase oral compositions also include compositions where the phases are multi-continuous including bi-continuous, layered, striped, marbled, ribbons, swirled, and combinations thereof.

The term "emulsion" as understood herein is an example of a multi-phase composition wherein: 1) at least one of the phases is discontinuous and 2) at least one of the phases is continuous. Examples of emulsions include droplets of water dispersed in oil. In this example the water and oil would be mutually immiscible with each other, water would be the discontinuous phase, and the oil would be the continuous phase.

The term "water-in-oil emulsion" as understood herein is an example of an emulsion wherein 1) the discontinuous phase is aqueous, and 2) the continuous phase is hydrophobic.

The term "aqueous phase" as understood herein is at least one hydrophilic phase that comprises water and an active agent (e.g. bleaching agent), and is immiscible with the hydrophobic phase. In certain embodiments, each part of the aqueous phase contains at least 2% of the active agent by weight of the aqueous phase. Optionally the aqueous phase may further comprise ingredients that are water soluble, water miscible, or combinations thereof, such as for example water soluble solvents, alcohol, polyethylene glycol, carbopol, etc. or mixtures thereof. In some embodiments, if and when immiscible fillers are added to the aqueous phase, the percentage of the aqueous phase in the composition is calculated by excluding the immiscible filler.

The term "hydrophobic phase" as understood herein means all components of the composition that are immiscible with the hydrophilic phase (e.g. aqueous phase). In certain embodiments the hydrophobic phase may further comprise ingredients that are soluble, miscible or combinations thereof in the hydrophobic phase, such as for example hydrocarbon solvents dissolved into the hydrophobic phase, polyethylene dissolved into the hydrophobic phase, microcrystalline wax dissolved into the hydrophobic phase, or mixtures thereof.

The term "particle" as used herein is a discrete, solid or semisolid material. Solid particles have dimensions larger than individual atoms or molecules and are typically submicron to about a millimeter in their largest dimension. In certain embodiments, particles may be agglomerated into an agglomerate of discrete particles. In certain embodiments particles may have dimensions or a number-average equivalent-diameter or volume-average equivalent-diameter from about 50 nm to about 1 mm.

The term "hydrophilic bleaching agent particle" as used herein is a particle that a) comprises a bleaching agent, and b) is soluble in water, swells (increase in volume and/or weight) upon contact with water or releases a bleaching agent upon contact with water. If a bleaching agent is released, the bleaching agent may be a gas, liquid, or solid dissolved in a liquid. In certain embodiments the hydrophilic bleaching agent particle is insoluble in the hydrophobic phase. In certain embodiments the hydrophilic bleaching agent particles or multi-phase oral composition may further comprise ingredients that are water soluble, water miscible, or combinations thereof, such as for example water water-soluble solvents, alcohols, carbopol, polyalkylene glycols, humectants, glycerin, sorbitol, xylitol, butylene glycol, polyethylene glycol, and propylene glycol, and mixtures thereof. In certain embodiments, the hydrophilic bleaching agent particles may also include water of hydration or solvents of crystallization. If these ingredients are added to or present in the hydrophilic bleaching agent particles, the percentage of the hydrophilic bleaching agent particles in the composition is calculated by excluding these ingredients. If water-insoluble or water-immiscible fillers are added to the hydrophilic bleaching agent particles or oral composition, the percentage of the hydrophilic bleaching agent particles in the composition is calculated by excluding these fillers.

Oral Care Product

The oral care product of the present invention is used by consumers to apply an oral care composition, preferably a leave-on composition, to the teeth or gums of the consumer. The product can be conveniently used at home by the consumer. The oral care product comprises a package containing an oral care composition, as described herein.

Package

The package utilized in the oral care product of the present invention comprises an applicator tip attached to a container formed of a substrate comprising one or more layers, preferably made of a polyolefin-based material. The applicator tip has a dispensing orifice in fluid communication with the container and comprises a material having a Shore A hardness of from about 15 to about 80. Preferably, the applicator tip comprises a plurality of columnar projections as described herein. Preferably, the substrate forming the container is an oxygen-permeable substrate, wherein the substrate has an oxygen transmission rate at 23° C. of at least about 5 cc/(m2*day), especially when the oral care composition comprises a peroxide bleaching agent. The package further comprises a cap covering the dispensing orifice.

Applicator Tip

The package of the present invention comprises an applicator tip which comprises a dispensing orifice. The dispensing orifice is in fluid communication with the container of the package, which contains the oral care composition of the present invention.

The applicator tip is preferably made of a material selected from food & drug grade materials, materials on the GRAS (Generally Regarded As Safe) list, or other applicable materials approved for use within the oral cavity according to local laws.

The applicator tip can be made from any suitable material, such as for example, a polymer, an elastomer, silicone resin, rubber, and/or combinations thereof.

Suitable polymer materials include, but are not limited to, polypropylene, polyethylene, polyethylene terephthalate, and/or combinations thereof.

Suitable elastomer materials include, but are not limited to, thermoplastic elastomers, a styrenic, a copolyester, a polyurethane, a polyamide, a polyolefin blend, a polyolefin alloy, a reactor TPO, a polyolefin plastomer, a polyolefin elastomer, and/or combinations thereof. Suitable elastomers include, for example, an elastomer made from PolyOne® under the Versaflex™ or Dynaftex™ product lines, from Hapco, Inc under the Steralloy™ product line, or from United Soft Plastics under the Unison Standard SEBS-based thermoplastic elastomer.

Preferably, the applicator tip is made of a silicone resin.

The applicator tip will have a tooth-contacting surface, which contacts the teeth of a consumer during application of the oral care composition from the package of the present invention. The tooth-contacting surface is preferably substantially planar (e.g. substantially flat) and surrounds the dispensing orifice of the applicator tip. By "substantially planar" or "substantially flat" it is meant that a majority of the tooth-contacting surface is planar or flat, e.g. allowing for the edges of the surface to be curved or beveled.

In one aspect, the tooth-contacting surface forms an acute angle with respect to the longitudinal axis of the applicator tip. The angle formed between the tooth-contacting surface and the longitudinal axis of the applicator tip is preferably from about 20° to about 80°, preferably from about 30° to about 60°, or preferably from about 40° to about 50°.

The tooth-contacting surface of the applicator tip preferably has a surface area of from about 30 to about 80 square millimeters, preferably from about 40 to about 70 square millimeters, or preferably from about 50 to about 60 square millimeters. If the tooth-contacting surface comprises projections extending therefrom, the surface area covered by the base of the projections is counted as part of the surface area of the tooth-contacting surface.

The applicator tip of the present invention can exhibit a ratio of surface area of tooth-contacting surface to area of dispensing orifice within a range of from about 10 to about 30, preferably from about 15 to about 25, and preferably from about 17 to about 20.

In one aspect, the tooth-contacting surface is substantially planar and is free of projections extending therefrom.

In one aspect, the tooth-contacting surface comprises a plurality of columnar projections extending therefrom.

Durometer

The applicator tip is preferably made of a relatively soft and/or flexible material. The soft, flexible applicator tip of the package of the present invention provides effective spreading of the oral care composition of the present invention onto teeth during use, especially wherein the composition has a cone penetration consistency value of from about 10 to about 500, preferably from about 100 to about 300.

As such, the applicator tip is preferably made of a material having a durometer exhibiting a Shore A hardness value of from about 15 to about 80, from about 25 to about 80, from about 25 to about 70, from about 30 to about 70, or from about 45 to about 70. The Shore A hardness of the material forming the applicator tip is determined according to ASTM Test No. D2240, which is herein incorporated by reference.

Columnar Projections

The applicator tip optionally, but preferably, comprises a plurality of columnar projections extending from the tooth-contacting surface of the applicator tip. The columnar projections are preferably integrally molded with the applicator tip, and of the same material as the applicator tip. As used herein, the term "columnar" refers to projections that resemble columns Such columnar projections can be cylindrical, e.g. having a circular cross-sectional shape, or other cross-sectional shapes such as square, rectangular, oval, star-shaped, or the like.

The applicator tip preferably comprises at least 0.1, preferably at least 0.2, and more preferably at least 0.3 columnar projections per square millimeter of tooth-contacting surface of the applicator tip. Preferably the applicator tip comprises from about 0.1 to about 1, preferably from about 0.1 to about 0.5, and more preferably from about 0.2 to about 0.4 columnar projections per square millimeter of tooth-contacting surface of the applicator tip.

The columnar projections will typically have a mean average height (measured from the proximal base of the projection at the tooth-contacting surface to the distal end of the projection) of from about 0.3 to about 1.7 mm, preferably from about 0.5 to about 1.5 mm, or preferably from about 1 to about 1.4 mm.

The columnar projections will typically have a mean average minimum diameter of from about 0.1 mm to about 2 mm, from about 0.3 mm to about 1.5 mm, or preferably from about 0.7 mm to about 1.2 mm. The minimum diameter is the shortest distance measured between two points opposite each other along the perimeter of the columnar projection. If the columnar projection is cylindrical (i.e. having a circular cross-section), the minimum diameter is the diameter of the circular cross-section of the cylindrical columnar projection.

The distal end of each projection can be blunt, rounded, or the like, preferably slightly rounded.

It is generally preferred for the applicator tip to comprise a plurality of columnar projections, as such columnar projections can improve the spreading and evenness of application of the oral care composition onto the teeth of the consumer.

Dispensing Orifice

The applicator tip comprises a dispensing orifice which will typically have a minimum diameter of at least about 0.5 mm, preferably at least about 1 mm, preferably at least about 1.5 mm, or preferably at least about 2 mm. The dispensing orifice will preferably have a minimum diameter of from about 0.5 mm to about 10 mm, or preferably from about 1 mm to about 5 mm, or preferably from about 1 mm to about 3 mm. The minimum diameter is the shortest distance measured between two points opposite each other along the perimeter of the orifice. If the orifice is circular, the minimum diameter is the diameter of the circular orifice. The orifice can be in a variety of shapes, including circular, oval, rectangular, star-shaped, and the like.

The minimum diameter of the dispensing orifice can be important depending on the nature of the multi-phase oral composition. For example, when the multi-phase oral composition has a cone penetration consistency value of from about 10 to about 500, or from about 100 to about 300, the dispensing orifice preferably has a minimum diameter of at least about 1 mm, preferably at least about 1.75 mm, and preferably at least about 2 mm.

In one aspect, the dispensing orifice is a ribbon orifice having an oval or rectangular shape. Such a ribbon orifice is described in detail in U.S. application Ser. No. 16/898,471, filed Jun. 11, 2020, which is incorporated by reference herein.

Suitable applicator tips are shown in FIGS. 1A-1B and 2A-2B. The applicator tip of FIGS. 1A-1B comprises a plurality of columnar projections, whereas the applicator tip of FIGS. 2A-2B does not.

Figure 1B:
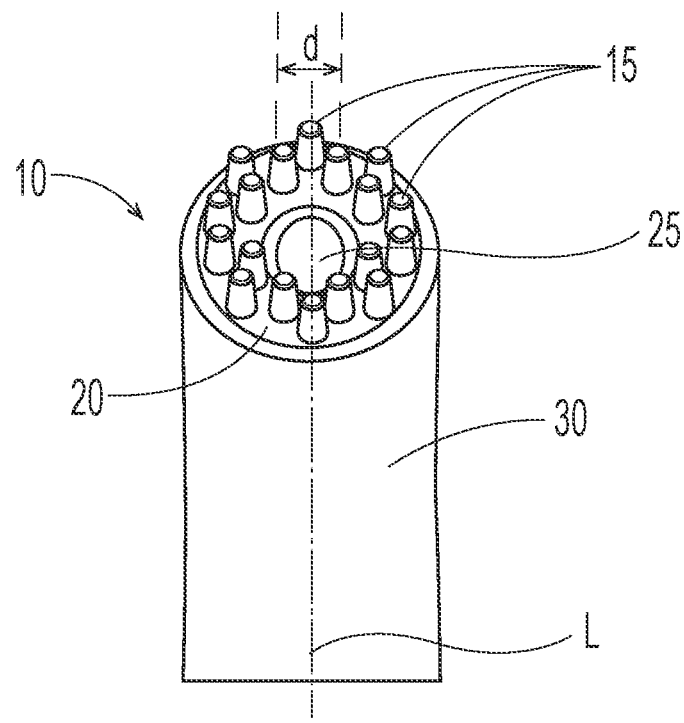
FIG. 1B is a front view of the applicator tip of FIG. 1A.

The applicator tip 10 of FIGS. 1A-1B comprises a plurality of columnar projections 15 extending from a tooth-contacting surface 20 of the applicator tip 10. The tooth-contacting surface forms an angle (a) with respect to a longitudinal axis L of the applicator tip 10 of about 45°. The tooth-contacting surface 20 surrounds a dispensing orifice 25, which has a minimum diameter (d) of about 2 mm. The applicator tip 10 is made of a silicone resin material 30. The applicator tip 10 is fitted over a holder element 35 which is made of a linear low density polyethylene material. The applicator tip 10 is attached to the container (not shown) via the holder element 35, which is more rigid than the applicator tip 10.

Figure 2A:
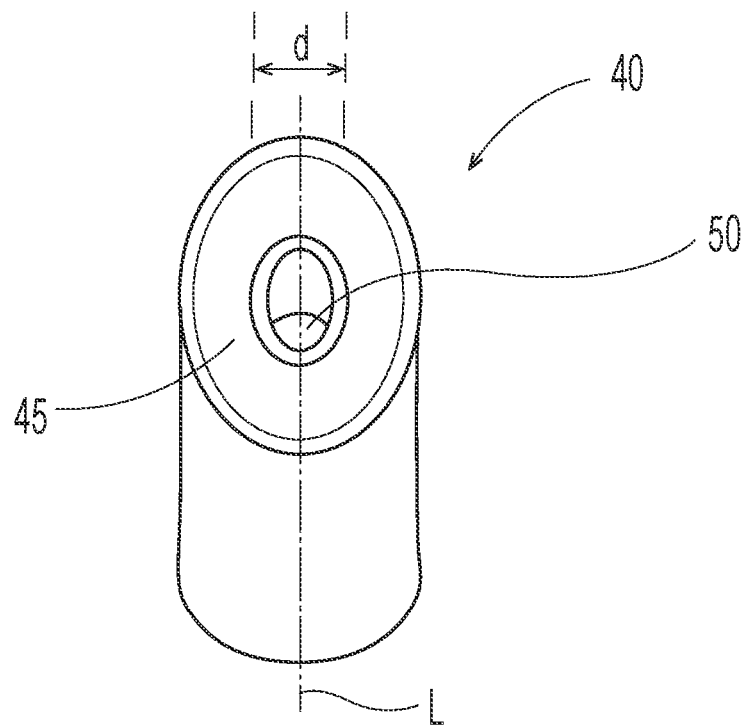
FIG. 2A is a perspective view of another embodiment of an applicator tip of the present invention.
Figure 2B:
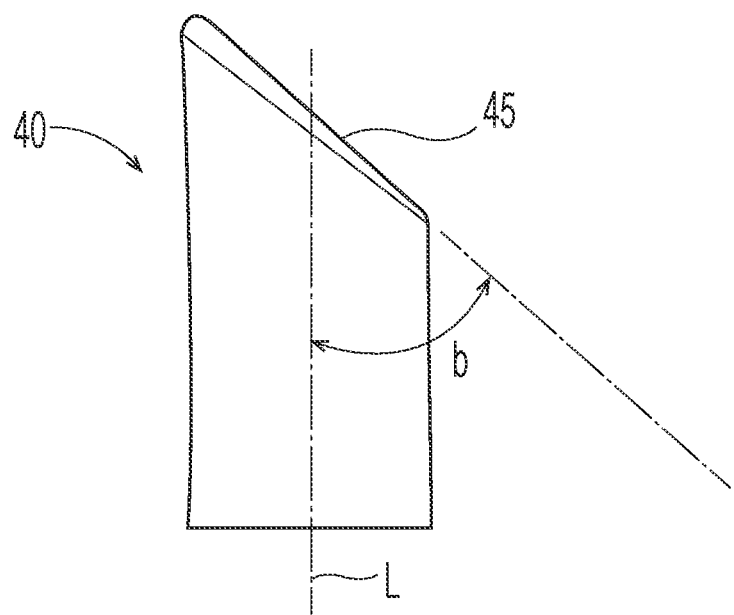
FIG. 2B is a side view of the applicator tip of FIG. 2A.

The applicator tip 40 of FIGS. 2A-2B comprises a tooth-contacting surface 45 which surrounds a dispensing orifice 50 having a minimum diameter (d) of about 2 mm. The tooth-contacting surface 45 forms an angle (b) with respect to the longitudinal axis L of the applicator tip 40 of about 45°. The applicator tip 40 is made of a silicone resin material.

Container

The applicator tip of the present invention is attached to a container of the package, wherein the dispensing orifice of the applicator tip is in fluid communication with the container. The container contains the oral care composition of the present invention. The container is formed of a substrate as described hereinbelow.

Substrate

The container of the present invention is formed of a substrate comprising one or more layers. The layer(s) of the substrate will typically comprise a polyolefin-based material. By "polyolefin-based material" it is to be understood herein that all different types of polyolefins and metallocene resins well known in the art including the polyolefin copolymers having (Actinic monomers such as ethylene, propylene, butene, and the like, are suitable. Preferred herein are polyethylenes such as low density polyethylene (LOPE), linear low density polyethylene (LLDPE), high density polyethylene (HDPE), and the like, and combinations thereof. Such polyethylenes are known to those skilled in the art and are commercially available, for example, from Dow Chemical and Shell Petrochemical.

The layer(s) of polyolefin-based material can be blended, laminated (e.g. via adhesive), and/or coextruded together, Preferred herein are laminated or coextruded materials comprising a low density polyethylene, a linear low density polyethylene, a high density polyethylene, or mixtures thereof. The substrates can have different thicknesses and densities depending on their use.

The substrate can comprise one layer, two layers, three layers, four layers, or more than four layers. In one aspect, the substrate comprises two layers or three layers.

The substrate can have an overall thickness of from about 0.1 mm to about 2 mm, preferably from about 0.2 mm to about 0.6 mm. The thickness of each layer can be from about 0.003 mm to about 1 mm, preferably from about 0.1 mm to about 0.3 mm.

The substrate can be supplied as a sheet of material, which can then be formed into a container using conventional methods. The container can be in a variety of forms, most commonly in the form of a tube. A tube will typically have one end that is sealed, e.g. crimped and/or heat-sealed, and one end having an orifice for dispensing the composition contained in the container. The orifice of the tube is typically covered by a cap, which can be a removable cap (e.g. threaded cap or pull-off cap) or a flip-top cap having a hinge.

The substrate can further comprise colorant, such as dyes or pigments, to impart a desired color to the substrate.

The outer surface of the substrate can be decorated using inks, metallic hot stamping foil, and/or matte or gloss varnishes.

The container formed from the substrate can be in a variety of forms, including a tube or bottle, and preferably a tube having a seal at one end of the tube and the dispensing orifice at the opposite end of the tube.

Oxygen Transmission Rate (OTR)

The substrate used to form the container of the present invention can be an oxygen-permeable substrate. An oxygen-permeable substrate can be preferred, especially if the multi-phase oral composition contained within the container comprises a peroxide material. A suitable oxygen-permeable substrate will typically have an oxygen transmission rate (OTR) that is suitable to facilitate a sufficient amount of oxygen generated inside the container to diffuse through the substrate to prevent expansion of the container during storage due to oxidation of the peroxide contained in the tooth whitening composition of the present invention. The substrate will therefore have an OTR of at least about 5 cubic centimeters per square meter per day ($cc/(m^2*day)$), at least about 10 $cc/(m^2*day)$, at least about 20 $cc/(m^2*day)$, at least about 50 $cc/(m^2*day)$, at least about 100 $cc/(m^2*day)$, or at least about 200 $cc/(m^2*day)$. Preferably, the substrate will have an OTR of from about 5 to about 500 $cc/(m^2*day)$, from about 10 to about 300 $cc/(m^2*day)$.

The OTR of a sample of the oxygen-permeable substrate is measured according to ASTM D3985 ("Standard Test Method for Oxygen Gas Transmission Rate Through Plastic Film Sheeting Using Coulometric Sensor"). Such an OTR measurement can be made using an Oxtran 2/21 Oxygen Permeability Instrument available from MOCON Laboratory (Minneapolis, Minnesota, USA).

Barrier Layer

The substrate used to form the container of the present invention may comprise a barrier layer, or may be free of a barrier layer. Barrier layers are commonly used in cosmetic or toothpaste tubes to better isolate the composition contained within such tubes from the environment to improve stability of the composition during storage. As such, more volatile components of the composition, such as flavors or perfumes, will tend to be more stable, as well as other components that may tend to react with environmental components. Barrier layers will typically have an oxygen transmission rate (OTR) of less than about 5, less than about 4, less than about 3, less than about 2, less than about 1, or less than about 0.5 $cc/(m2*day)$ at 23° C., as measured according to ASTM D3985. Therefore, substrates which contain a barrier layer will therefore have an OTR which is the same as, or less than, the OTR of the barrier layer.

However, when a composition contained within a container having a barrier layer comprises a peroxide material (especially in aqueous form or within an aqueous phase of the composition), the container having a barrier layer can suffer from unacceptable expansion of the container during storage of the composition due to a level of oxidation of the peroxide material over time in storage. This can lead to the container looking unsightly (e.g. bloated) or even leakage of the composition from the container due to failure of seals of the container resulting from the expansion of the container. As such, there is a need to maintain stability of the composition contained within the container while preventing bloating of the package and leakage of the composition from the package.

Examples of barrier layers, which are not present in the substrate which forms the container herein, include an aluminum barrier layer (ABL) and a plastic barrier layer (PBL), such as an ethyl vinyl alcohol barrier layer.

Oral Care Composition

The oral care composition of the present invention comprises an oral care active and has a cone penetration value of from about 10 to about 500. The oral care compositions of the present invention can be applied to the surface of teeth, gums, cheeks, tongue, or any other oral cavity surface.

In one aspect, the oral care composition is a leave-on composition.

Oral Care Active

Suitable oral care active agents for incorporation in the oral care compositions of the present invention include those described in detail in U.S. Patent App. Pub. No. 2018/0133119 and U.S. Patent App. Pub. No. 2018/0133121. Suitable active agents include bleaching agents, one or more anticalculus agent(s), a fluoride ion source, antimicrobial agent(s), dentinal desensitizing agent(s), anesthetic agent(s), antifungal agent(s), anti-inflammatory agent(s), selective H-2 antagonist(s), anticaries agent(s), nutrient(s), erythritol, probiotics, and mixtures thereof. Specific examples of active agents include, but are not limited to, hydrogen peroxide, fluoride salts, stannous salts, zinc salts, oxalates, cetylpyridinium chloride and mixtures thereof. One of the purposes of the oral care compositions can be to deliver an active agent for a sufficient period of time to achieve a benefit of the active agent. For example, if the active agent is hydrogen peroxide, the composition needs to contact the surface of teeth for a sufficient period of time to whiten the teeth. If the active agent is stannous fluoride, the composition needs to contact the surface of teeth and/or gums for a sufficient period of time to deposit stannous ions and/or fluoride ions to provide an antigingivitis, antisensitivity, and/or anticaries benefit.

Cone Penetration Consistency Value

The oral care composition, such as a multi-phase oral composition, will have a cone penetration consistency value within certain ranges. The cone penetration consistency value of the oral care composition can be a factor to ensure that the oral care composition: 1) is substantive and does not run down the teeth or run off of the applicator tip during application or during use; and 2) releases an effective amount of the bleaching agent or active agent during use. Specifically, if the cone penetration consistency value of the oral care composition is too high, the oral care composition may not be substantive and run down the teeth or run out of the delivery carrier during application or during use. In contrast, if the cone penetration consistency value of the oral care composition is too low, the oral care composition may not release an effective amount of the bleaching agent or active agent during use, and/or be difficult to dispense from the package of the present invention. In certain aspects, the cone penetration consistency value of the oral care compositions may be in the range of from about 10 to about 500, preferably in the range of from about 100 to about 300, preferably in the range from about 150 to about 250, and more preferably in the range of from about 170 to about 200 or any other numerical range, which is narrower and which falls within such broader numerical range, as if such narrower numerical ranges were all expressly written herein, as measured according to ASTM method D937-07. In certain embodiments, the cone penetration consistency value of the multi-phase oral composition may be from about 10, 25, 50, 100, 110, 120, 130, 140, 150, 160, 170, 180, 190, 200, 210, 220, 230, 240, 250, 300, 400, or 500, to about 25, 50, 100, 110, 120, 130, 140, 150, 160, 170, 180, 190, 200, 210, 220, 230, 240, 250, 300, 400, or 500, or any other numerical range, which is narrower, and which falls within such broader numerical range, as if such narrower numerical ranges were all expressly written herein as measured according to ASTM method D937-07.

Suitable oral care compositions for containing in the container of the package of the present invention include those described in detail in US 2018/0133119 A1; U.S. application Ser. Nos. 16/850,033 and 16/850,035, filed Apr. 16, 2020; U.S. application Ser. No. 16/842,800, filed Apr. 8, 2020; and U.S. application Ser. Nos. 16/899,834, 16/899,882, and 16/899,919, filed Jun. 12, 2020; which are each incorporated by reference herein.

In one aspect, the oral care composition of the present invention is a multi-phase oral composition.

Multi-Phase Oral Composition

Suitable multi-phase oral compositions comprise a hydrophobic phase and a hydrophilic phase. The multi-phase oral composition is preferably in the form of an emulsion. Examples of multi-phase oral compositions in the form of an emulsion include oil-in-water emulsions, water-in-oil-in-water emulsions, and oil-in-water-in-oil emulsions. The multi-phase oral composition can also include compositions wherein the phases are multi-continuous (including bi-continuous), layered, striped, marbled, ribbons, swirled, and combinations thereof.

The multi-phase oral composition comprises an oral care active, as described herein. The oral care active can be comprised in the hydrophilic phase, the hydrophobic phase, or both.

In one aspect, the multi-phase oral composition comprises flavor and a peroxide bleaching agent, preferably wherein the hydrophobic phase comprises flavor and the hydrophilic phase comprises peroxide bleaching agent.

Hydrophobic Phase

The hydrophobic phase of the multi-phase oral composition comprises flavor to impart a pleasant taste and/or odor during use of the composition by a consumer. The hydrophobic phase of the composition can help to protect and stabilize the flavor in a tooth whitening product, especially wherein the package of the tooth whitening product does not include a barrier layer. Barrier layers, such as aluminum barrier layer or plastic barrier layers (e.g. ethyl vinyl alcohol), can be incorporated in packages of the present invention to help stabilize ingredients such as flavors, especially when used to package compositions that are not multi-phase or do not contain a peroxide material.

In one aspect, the package of the present invention is free of a barrier layer. In such case, incorporating the flavor in the hydrophobic phase of the composition can help to protect and stabilize the flavor during storage. In this regard, the flavor is preferably dispersed in the hydrophobic phase, and is preferably premixed with other hydrophobic phase component(s) before combining with hydrophilic phase component(s). In one aspect, for example, if the hydrophobic phase comprises petrolatum, the flavor is premixed with the petrolatum before combining with the hydrophilic phase component(s).

Suitable flavors can comprise oil of wintergreen, oil of peppermint, oil of spearmint, clove bud oil, menthol, anethole, methyl salicylate, eucalyptol, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal (known as CGA), and mixtures thereof. Preferably, the flavor comprises menthol. The flavor is generally used at levels of from about 0.01% to about 5%, in particular from about 0.1% to about 3%, more particular from about 0.3% to about 2%, by weight of the composition.

The hydrophobic phase can comprise non-toxic edible oils, saturated or unsaturated fatty alcohols, aliphatic hydrocarbons, long chain triglycerides, fatty esters, and mixtures thereof. In certain aspects, the hydrophobic phase may also comprise silicones, polysiloxanes, and mixtures thereof. In certain aspects, the hydrophobic phase may be selected from mineral oil, petrolatum, and mixtures thereof. Preferably the hydrophobic phase comprises petrolatum, e.g. white petrolatum. Examples of petrolatum include Snow White Pet—C from Calumet Specialty Products (Indianapolis, IN) G-2191 from Sonneborn (Parsippany, NJ), G-2218 from Sonneborn, G-1958 from Sonneborn, G-2180 from Sonneborn, Snow White V28 EP from Sonneborn, and Snow White V30 from Sonneborn, and mixtures thereof. Preferably, the hydrophobic phase comprises at least about 30%, at least about 50%, at least about 60%, or at least about 70%, by weight of the hydrophobic phase, of petrolatum.

The multi-phase oral composition of the present invention will typically comprise hydrophobic phase at a level of at least about 30%, at least about 40%, at least about 50%, at least about 60%, at least about 70%, at least about 80%, or at least about 90%, by weight of the multi-phase composition; up to no more than about 99%, no more than about 95%, or no more than about 90%, by weight of the multi-phase oral composition.

The hydrophobic phase will preferably have a cone penetration consistency value within a certain range to provide improved protection and stabilization of the flavor, and release an effective amount of the bleaching agent or active agent during use. The cone penetration consistency value of the hydrophobic phase may be in the range of from about 100 to about 500, preferably in the range from about 150 to about 250, and more preferably in the range of from about 170 to about 200 or any other numerical range, which is narrower and which falls within such broader numerical range, as if such narrower numerical ranges were all expressly written herein, as measured according to ASTM method D937-07. In certain aspects, the cone penetration consistency value of the hydrophobic phase may be from about 10, 25, 50, 100, 110, 120, 130, 140, 150, 160, 170, 180, 190, 200, 210, 220, 230, 240, 250, 300, 400, or 500, to about 25, 50, 100, 110, 120, 130, 140, 150, 160, 170, 180, 190, 200, 210, 220, 230, 240, 250, 300, 400, or 500, or any other numerical range, which is narrower, and which falls within such broader numerical range, as if such narrower numerical ranges were all expressly written herein as measured according to ASTM method D937-07.

Hydrophilic Phase

The hydrophilic phase of the multi-phase oral compositions can comprise a peroxide bleaching agent. In one aspect, the hydrophilic phase comprises an aqueous phase comprising the peroxide bleaching agent, preferably hydrogen peroxide. In this aspect, the aqueous phase can comprise hydrogen peroxide at a level of from about 2%, 5%, 8.75%, 10%, 15%, 17.5%, 20%, 25%, 30%, 35%, 45%, 50%, 60%, or 67% to about 67%, 60% to about 50%, 45%, 40%, 35%, 30%, 25%, 20%, 17.5%, 15%, 10%, 8.75%, or 5%, by weight of the aqueous phase, or any other numerical range, which is narrower and which falls within such broader numerical range, as if such narrower numerical ranges were all expressly written herein.

The total level of peroxide bleaching agent in the multi-phase oral composition can be from about 0.001%, 0.01%, 0.02%, 0.03%, 0.04%, 0.05%, 0.06%, 0.07%, 0.08%, 0.09%, 0.095% 0.099995%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15% or 20%, to about 0.1%, 1%, 5%, 10%, 15% or 20%, by weight of the multi-phase oral composition, or any other numerical range, which is narrower and which falls within such broader numerical range, as if such narrower numerical ranges were all expressly written herein.

In one aspect, the composition is an emulsion, preferably a water-in-oil emulsion, wherein the aqueous phase is discontinuous and is dispersed as droplets within the hydrophobic phase, which is continuous. The size of the droplets of the aqueous phase can be a factor in decreasing oral/topical irritation and/or tooth-sensitivity. If the size of the droplets of the aqueous phase is too large it may lead to large spots on oral/topical/tooth surfaces that are exposed to a high concentration of the bleaching agent, which in turn may lead to oral/topical irritation and/or tooth-sensitivity.

In one aspect, the number-average equivalent-diameter or volume-average equivalent-diameter of the droplets of aqueous phase may be from 0.001 micron, 0.01 micron, 0.1 micron, or 1 micron, up to no more than about 0.001 micron, 0.01 micron, 0.1 micron, 1 micron, 5 microns, 10 microns, 50 microns, 100 microns, 500 microns, or 1000 microns or any other numerical range, which is narrower and which falls within such broader numerical range, as if such narrower numerical ranges were all expressly written herein.

Compositions that have a high density of large droplets of aqueous phase may lead to oral/topical irritation and/or tooth-sensitivity. In one aspect, the "two-dimensional density of droplets" of aqueous phase with a cross-sectional area larger than about 1000, 3000, 10000, 20000, or 50000 square microns may be no more than about 0.5, 1, 2, 3, 4, 5, 6, 7, 8, 9, 10, 15, 20, 25, 50, or 100 per square centimeter of the two-dimensional plane, or any other numerical range, which is narrower and which falls within such broader numerical range as if such narrower numerical ranges were all expressly written herein. The procedure to measure the two-dimensional density of droplets is described in detail in US 2018/0133119 A1, which is incorporated by reference herein.

The hydrophilic phase can comprise hydrophilic bleaching agent particles. Examples of suitable hydrophilic bleaching agent particles include urea peroxide, and complexes of hydrogen peroxide and polyvinylpyrrolidone polymers. In one aspect, the hydrophilic bleaching agent particles can constitute the hydrophilic phase itself (i.e. the hydrophilic phase consists of hydrophilic bleaching agent particles). In certain aspects, the hydrophilic bleaching agent particles may be from about 0.6% to about 10%, or from about 0.6% to about 6%, or from about 1% to about 5%, or from about 1% to about 3% by weight of the multi-phase oral composition, or any other numerical range, which is narrower and which falls within such broader numerical range, as if such narrower numerical ranges were all expressly written herein. Multi-phase oral compositions comprising hydrophilic bleaching agent particles suitable for the present invention are described in detail in U.S. application Ser. No. 16/842,800, filed Apr. 8, 2020, which is incorporated by reference herein.

Emulsifier

The compositions of the present invention can optionally further comprise an emulsifier. In one aspect, the composition can comprise from about 0.001% to about 30%, by weight of the composition, of emulsifier. In certain aspects, the composition can comprise from about 0 to about 0.1%, from about 0.1% to about 5%, from about 0.1% to about 3%, or from about 0.5% to about 1.5%, by weight of the composition, of emulsifier. In one aspect, the composition is free of emulsifier.

Preferred emulsifiers, especially for multi-phase oral compositions in the form of a water-in-oil emulsion, include those having a hydrophilic-lipophilic balance (HLB) value of from about 1 to about 10, an HLB value of from about 3 to about 8, an HLB value from about 4 to about 7, or an HLB from about 4 to about 6.

Suitable emulsifiers can include (i) natural emulsifying agents, such as acacia, gelatin, lecithin and cholesterol; (ii) finely dispersed solids, such as colloidal clays, bentonite, veegum, magnesium aluminum silicate; and (iii) synthetic emulsifying agents, such as salts of fatty acids, sulfates such as sorbitan trioleate, sorbitan tristearate, sucrose distearate, propylene glycol monostearate, glycerol monostearate, propylene glycol monolaurate, sorbitan monostearate, sorbitan monolaurate, polyoxyethylene-4-lauryl ether, sodium lauryl sulfate, sulfonates such as dioctyl sosium sulfosuccinate, glyceryl esters, polyoxyethylene glycol esters and ethers, diethylene glycol monostearate, PEG 200 distearate, and sorbitan fatty acid esters, such as sorbitan monopalmitate, and their polyoxyethylene derivatives, polyoxyethylene glycol esters such as the monostearate, Polysorbate 80 (ethoxylated sorbitan monooleate); and mixtures thereof.

Sweetening Agent

The composition of the present invention can optionally further comprise a sweetening agent such as sucralose, sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and mixtures thereof. If present, the composition contains from about 0.1% to about 10% of sweetening agent, in particular from about 0.1% to about 1%, by weight of the composition.

Suitable multi-phase oral compositions in the form of emulsions, such as water-in-oil emulsions, are described in detail in US 2018/0133119 A1, which is incorporated by reference herein. Suitable multi-phase oral compositions in the form of jammed oil-in-water emulsions are described in detail in U.S. application Ser. Nos. 16/850,033 and 16/850,035, filed Apr. 16, 2020, which are incorporated by reference herein. Suitable multi-phase oral compositions comprising hydrophilic bleaching agent particles are described in detail in U.S. application Ser. No. 16/842,800, filed Apr. 8, 2020, which is incorporated by reference herein.

Figure 3:
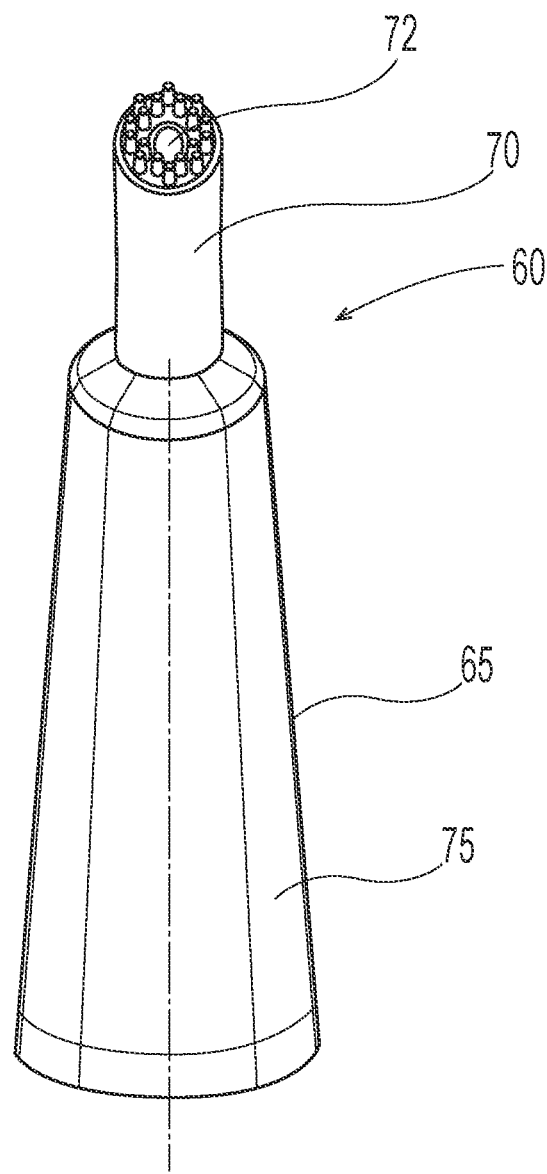
FIG. 3 is a perspective view of an embodiment of a package of the present invention.

FIG. 3 shows a package 60 of the present invention comprising a container 65 in the form of a tube and comprising an applicator tip 70 as shown in FIGS. 1A-1B. The package further comprises a cap (not shown) removably covering the applicator tip 70, which cap comprises a pin shaped to insert into and seal the dispensing orifice 72 when the cap is put on the package.

Figure 4:
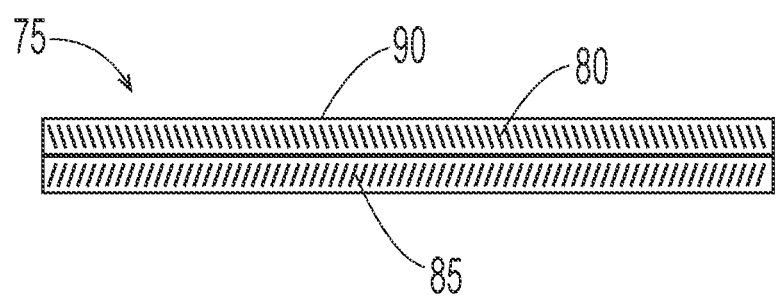
FIG. 4 is a cross-sectional view of an oxygen-permeable substrate of the present invention.

An oxygen-permeable substrate 75 is used to form the container comprises two layers, which are co-extruded, as shown in FIG. 4. The first layer 80, which faces the external environment, comprises about 50% LDPE, about 50% LLDPE, and a minor amount of colorant. The second layer 85, which faces the tooth whitening composition contained inside the container, comprises about 45% HDPE, about 45% LLDPE, about 10% of polyolefin copolymer, and a minor amount of colorant.

The outer surface 90 of the first layer 80 of the container 65 can be decorated using inks, metallic hot stamping foil, and/or matte or gloss varnishes (not shown).

The oxygen transmission rate of a sample of the oxygen-permeable substrate 75 is measured according to ASTM D3985 using an Oxtran 2/21 Oxygen Permeability Instrument available from MOCON Laboratory (Minneapolis, Minnesota, USA), with the following results:

| Oxygen Transmission Rate | | Steady State or |
|---|---|---|
| Replicate | cc/(m$^2$*day) | Test Duration* |
| A | 237 | Steady State |
| B | 242 | Steady State |

* The maximum test duration is 120 hours.

Such a package 60 is preferably used for containing a multi-phase oral composition of the present invention comprising a peroxide bleaching agent, which results in an oral care product that does not suffer from undesirable expansion of the package during storage of the oral care product over time.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care product comprising:
   a package comprising:
      a container, wherein the container is made of an oxygen-permeable substrate having an oxygen transmission rate of at least 5 cc/(m$^2$*day); and
      an applicator tip attached to the container, wherein the applicator tip comprises a material having a Shore A hardness of from 15 to 80 and has a dispensing orifice in fluid communication with the container, the dispensing orifice having a minimum diameter of at least 0.5 mm; and
   an oral care composition contained within the container of the package, wherein the oral care composition comprises an oral care active and has a cone penetration value of from 10 to 500.

2. The oral care product of claim 1, wherein the minimum diameter is at least 1 mm.

3. The oral care product of claim 1, wherein the cone penetration value is from 100 to 300.

4. The oral care product of claim 1, wherein the applicator tip comprises a tooth-contacting surface surrounding the dispensing orifice.

5. The oral care product of claim 4, wherein the applicator tip has a longitudinal axis, wherein the tooth-contacting surface forms an angle relative to the longitudinal axis of from 20° to 80°.

6. The oral care product of claim 5, wherein the angle relative to the longitudinal axis is from 30° to 60°.

7. The oral care product of claim 6, wherein the angle relative to the longitudinal axis is from 40° to 50°.

8. The oral care product of claim 4, wherein the tooth-contacting surface has a surface area of from 30 to 80 square millimeters.

9. The oral care product of claim 8, wherein the surface area is from 40 to 70 square millimeters.

10. The oral care product of claim 4, wherein the applicator tip comprises a plurality of columnar projections extending from the tooth-contacting surface.

11. The oral care product of claim 10, wherein each of the plurality of columnar projections have a mean average height of from 0.3 to 1.7 mm.

12. The oral care product of claim 11, wherein the mean average height is from 0.5 to 1.5 mm.

13. The oral care product of claim 10, wherein each of the plurality of columnar projections have a mean average minimum diameter of from 0.1 mm to 2 mm.

14. The oral care product of claim 13, wherein the mean average minimum diameter is from 0.3 mm to 1.5 mm.

15. The oral care product of claim 4, wherein the applicator tip comprises at least 0.1 columnar projections per square millimeter of the tooth-contacting surface of the applicator tip.

16. The oral care product of claim 15, wherein the applicator tip comprises at least 0.2 columnar projections per square millimeter of the tooth-contacting surface of the applicator tip.

17. The oral care product of claim 1, wherein the package further comprises a holder element onto which the applicator tip attaches, wherein the holder element is attached to the container.

18. The oral care product of claim 1, wherein the package further comprises a cap comprising a pin, wherein the pin fits into and seals the dispensing orifice.

19. The oral care product of claim 1, wherein the oral care active is selected from the group consisting of bleaching agents, anticalculus agents, a fluoride ion source, antimicrobial agents, dentinal desensitizing agents, anesthetic agents, antifungal agents, anti-inflammatory agents, selective H-2 antagonists, anticaries agents, nutrients, erythritol, probiotics, and mixtures thereof.

20. The oral care product of claim 1, wherein the oral care active is a bleaching agent.

21. The oral care product of claim 20, wherein the bleaching agent is a peroxide bleaching agent.

22. The oral care product of claim 1, wherein the oral care composition is an emulsion.

23. The oral care product of claim 22, wherein the emulsion comprises a hydrophilic phase comprising a peroxide bleaching agent and a hydrophobic phase.

24. The oral care product of claim 23, wherein the emulsion is a water-in-oil emulsion, wherein the hydrophilic phase is dispersed as droplets within the hydrophobic phase.

25. The oral care product of claim 1, wherein the container is free of a barrier layer.

26. The oral care product of claim 1, wherein the oral care product is a tooth whitening product and the oral care composition is a tooth whitening composition.

27. The oral care composition of claim 1, wherein the oral care composition is a multi-phase oral composition comprising a hydrophobic phase comprising flavor and a hydrophilic phase comprising a peroxide bleaching agent.

* * * * *